US006329198B1

(12) United States Patent
King et al.

(10) Patent No.: US 6,329,198 B1
(45) Date of Patent: Dec. 11, 2001

(54) PRODUCTION AND USE OF HUMAN NM23 PROTEIN AND ANTIBODIES THEREFOR

(75) Inventors: Charles Richter King, Washington, DC (US); Patricia Schriver Steeg, Ellicott City; Lance A. Liotta, Potomac, both of MD (US)

(73) Assignee: The United States of America as represented by the Department of Secretary Health & Human Services, Washington, DC (US)

(*) Notice: Subject to any disclaimer, the term of this patent is extended or adjusted under 35 U.S.C. 154(b) by 0 days.

(21) Appl. No.: 09/335,948

(22) Filed: Jun. 18, 1999

Related U.S. Application Data

(60) Division of application No. 08/475,684, filed on Jun. 7, 1995, which is a division of application No. 07/806,932, filed on Dec. 11, 1991, which is a continuation-in-part of application No. 07/422,801, filed on Oct. 18, 1989, now abandoned.

(51) Int. Cl.[7] .............................. C12N 15/70; C07K 5/00
(52) U.S. Cl. .............................. 435/320.1; 530/300
(58) Field of Search .............................. 530/350; 435/69.1, 435/320.1

(56) References Cited

U.S. PATENT DOCUMENTS

| | | | |
|---|---|---|---|
| Re. 35,097 | 11/1995 | Steeg et al. | 536/23.5 |
| 4,677,058 | 6/1987 | Tryggvason et al. | 435/7 |
| 4,683,195 | 7/1987 | Mullis et al. | 435/6 |
| 4,808,528 | 2/1989 | Tryggvason et al. | 435/172.2 |
| 4,816,400 | 3/1989 | Tryggvason et al. | 435/219 |
| 5,049,662 | 9/1991 | Steeg et al. | 536/27 |
| 5,288,852 | 2/1994 | Yamada et al. | 530/351 |
| 6,087,125 * | 7/2000 | Bandman et al. | 435/69.1 |

FOREIGN PATENT DOCUMENTS

| | | |
|---|---|---|
| WO 86/03226 | 6/1986 | (WO) . |
| 0 303 233 | 8/1987 | (WO) . |
| WO 91/06664 | 5/1991 | (WO) . |
| WO 91/06671 | 5/1991 | (WO) . |

OTHER PUBLICATIONS

Hailat et al. "High Levels of p19/nm23 Protein in Neuroblastoma are Associated with Advanced Stage Disease and with N–myc Gene Amplification" *J. Clin. Invest.*88:341–345, 1991.
Pulido–Cejudo et al. "Characterization of the Active Oligomer of the Human NDP Kinase with Monoclonal Antibodies" *FASAB J* 3(3):A331, 1989.
Paul, W.W. *Fundamental Immunology* Second Ed. Raven Press p. 176, 1989.
Schubart et al. "Homology Between the cDNAs Encoding Phosphoprotein p19 and SCG10 Reveals a Novel Mammalian Gene Family Preferentially Expressed in Developing Brain" *DNA* 8(6):389–398, Jul. 1989.
Schubart, U.K. "Expression of Phosphoprotein p19 in Brain, Testis, and Neuroendocrine Tumor Cells" *J. Biol. Chem.*263(24):12156–12160, 1988.
Lam et al. Isolation and Kinetic Studies of Nucleoside Diphosphokinase from Human Platelets and Effects of cAMP Phosphodiesterase Inhibitors *Biochem. Pharmacol.*35(24):4449–55, 1986.
Yokoyama et al. "Complete recovery of the Phosphoenzyme–Forming Activity of Nucleoside–Diphosphate Kinases After Reconstitution of their Subunits" *FEBS Lett.*206(2):287–91, 1986.
Kipps et al. *Handbook of Experimental Immunology* D.M. Weir, Ed. Blackwell Sci. Pub. Oxford, England vol. 4 Chapter 108. pp. 108.1–108.9, 1986.
Rouse et al. *Handbook of Experimental Immunology* D.M. Weir, Ed. Blackwell Sci. Pub. Oxford, England vol. 4 Chapter 116.pp. 116.1–116.10, 1986.
Koyama et al. Nucleosidediphosphate Kinase from Ehrlich Ascites Tumor Cells *J. Biochem.*95:925–935, 1984.
Barnes, et al. "Rapid Communication: Low nm23 Protein Expression in Infiltrating Ductal Breast Carcinomas Correlates with Reduced Patient Survival," *Am. J. Pathol.*139(2): 245–50 (1991).
Bevilacqua, et al. "Association of Low nm23 RNA Levels in Human Primary Infiltrating Ductal Breast Carcinomas with Lymph Node Involvement and Other Histopathological Indicators of High Metastatic Potential," *J. Cancer Research* 49: 5185–90 (Sep. 1989).
Biggs, et al. "A Drosophila Gene That Is Homologous to a Mammalian Gene Associated with Tumor Metastasis Codes for a Nucleoside Diphosphate Kinase," *Cell* 933–940 (1990).
Gilles et al. "Nucleoside Diphosphate Kinase from Human Erythrocytes: Structural Characterization of the Two Polypeptide Chains Responsible for Heterogeneity of the Hexameric Enzyme," *J. Biol. Chem.*266(14): 8784–89 (1991).
Rosengard, et al. "Reduced Nm23/Awd protein in tumor metastasis and aberrant Drosophila Development," *Nature* 342: 177–80 (Nov. 1989).
Stahl, et al. "Identification of a Second Human nm23 Gene.nm23–H2," *Can. Res.*51: 445 (1991).
Steeg, et al. "Evidence for a Novel Gene Associated with Low Tumor Metastatic Potential,"0 *J. NCI* 80(3): 200–4 (Apr. 1988).
Presecan, et al. "Nucleoside diphosphate kinase from human erythrocytes: purification, molecular mass and subunit structure," *FEBS Letters* 250:(2): 629–31 (Jul. 1989).
Steeg, et al. Proceedings of the AACR, Symposium 11 31: 504–05 (Mar. 1990) Abstracts.
Stahl et al. Cancer Research 51:445–449. 1991.*

* cited by examiner

*Primary Examiner*—Eggerton A. Campbell
(74) *Attorney, Agent, or Firm*—Needle & Rosenberg, P.C.

(57) ABSTRACT

Human nm23 DNA and protein is disclosed as well as antibodies which recognize human nm23 protein. The DNA and antibodies may be used to detect nm23 in human tumors to predict the malignancy potential of such tumors.

4 Claims, 9 Drawing Sheets

BREAST

TOTAL CASES 48
INFORMATIVE 25
ALLELIC LOSS 16 (64 %)

LUNG

TOTAL CASES 20
INFORMATIVE 12
ALLELIC LOSS 5 (42%)

KIDNEY

| | | |
|---|---|---|
| TOTAL CASES | 25 | |
| INFORMATIVE | 10 | |
| ALLELIC LOSS | 2 | (20%) |

SEQUENCE LISTING

```
<160> NUMBER OF SEQ ID NOS: 6

<210> SEQ ID NO 1
<211> LENGTH: 152
<212> TYPE: PRT
<213> ORGANISM: Homo Sapiens

<400> SEQUENCE: 1

Met Ala Asn Leu Glu Arg Thr Phe Ile Ala Ile Lys Pro Asp Gly Val
 1               5                  10                  15

Gln Arg Gly Leu Val Gly Glu Ile Ile Lys Arg Phe Glu Gln Lys Gly
            20                  25                  30

Phe Arg Leu Val Ala Met Lys Phe Leu Arg Ala Ser Glu Glu His Leu
        35                  40                  45

Lys Gln His Tyr Ile Asp Leu Lys Asp Arg Pro Phe Phe Pro Gly Leu
    50                  55                  60

Val Lys Tyr Met Asn Ser Gly Pro Val Val Ala Met Val Trp Glu Gly
65                  70                  75                  80

Leu Asn Val Val Lys Thr Gly Arg Val Met Leu Gly Glu Thr Asn Pro
                85                  90                  95

Ala Asp Ser Lys Pro Gly Thr Ile Arg Gly Asp Phe Cys Ile Gln Val
            100                 105                 110

Gly Arg Asn Ile Ile His Gly Ser Asp Ser Val Lys Ser Ala Glu Lys
        115                 120                 125

Glu Ile Ser Leu Trp Phe Lys Pro Glu Glu Leu Val Asp Tyr Lys Ser
    130                 135                 140

Cys Ala His Asp Trp Val Tyr Glu
145                 150


<210> SEQ ID NO 2
<211> LENGTH: 176
<212> TYPE: PRT
<213> ORGANISM: Homo Sapiens

<400> SEQUENCE: 2

Arg Pro Arg Gly Gly Ile Pro Ser Ala Leu Pro Ala Gln Arg Arg Arg
 1               5                  10                  15

Pro Ala Pro Pro Ala Ser Arg Thr Met Ala Asn Leu Glu Arg Thr Phe
            20                  25                  30

Ile Ala Ile Lys Pro Asp Gly Val Gln Arg Gly Leu Val Gly Glu Ile
        35                  40                  45

Ile Lys Arg Phe Glu Gln Lys Gly Phe Arg Leu Val Ala Met Lys Phe
    50                  55                  60

Leu Arg Ala Ser Glu Glu His Leu Lys Gln His Tyr Ile Asp Leu Lys
65                  70                  75                  80

Asp Arg Pro Phe Phe Pro Gly Leu Val Lys Tyr Met Asn Ser Gly Pro
```

-continued

```
                85                  90                  95

Val Val Ala Met Val Trp Glu Gly Leu Asn Val Val Lys Thr Gly Arg
            100                 105                 110

Val Met Leu Gly Glu Thr Asn Pro Ala Asp Ser Lys Pro Gly Thr Ile
        115                 120                 125

Arg Gly Asp Phe Cys Ile Gln Val Gly Arg Asn Ile Ile His Gly Ser
    130                 135                 140

Asp Ser Val Lys Ser Ala Glu Lys Glu Ile Ser Leu Trp Phe Lys Pro
145                 150                 155                 160

Glu Glu Leu Val Asp Tyr Lys Ser Cys Ala His Asp Trp Val Tyr Glu
                165                 170                 175


<210> SEQ ID NO 3
<211> LENGTH: 670
<212> TYPE: DNA
<213> ORGANISM: Homo Sapiens

<400> SEQUENCE: 3

cggccacgag gcggaatccc ttctgctctc ccagcgcagc gccgccgccc ggcccctcca      60

gcttcccgga ccatggccaa cctggagcgc accttcatcg ccatcaagcc ggacggcgtg     120

cagcgcggcc tggtgggcga gatcatcaag cgcttcgagc agaagggatt ccgcctcgtg     180

gccatgaagt tcctccgggc ctctgaagaa cacctgaagc agcactacat tgacctgaaa     240

gaccgaccat tcttccctgg gctggtgaag tacatgaact cagggccggt tgtggccatg     300

gtctgggagg ggctgaacgt ggtgaagaca ggccgagtga tgcttgggga gaccaatcca     360

gcagattcaa agccaggcac cattcgtggg gacttctgca ttcaggttgg caggaacatc     420

attcatggca gtgattcagt aaaaagtgct gaaaaagaaa tcagcctatg gtttaagcct     480

gaagaactgg ttgactacaa gtcttgtgct catgactggg tctatgaata agaggtggac     540

acaacagcag tctccttcag cacggcgtgg tgtgtccctg gacacagctc ttcattccat     600

tgacttagag gcaacaggat tgatcattct tttatagagc atatttgcca ataaagcttt     660

tggaagccgg                                                            670


<210> SEQ ID NO 4
<211> LENGTH: 152
<212> TYPE: PRT
<213> ORGANISM: Homo Sapiens

<400> SEQUENCE: 4

Met Ala Asn Cys Glu Arg Thr Phe Ile Ala Ile Lys Pro Asp Gly Val
 1               5                  10                  15

Gln Arg Gly Leu Val Gly Glu Ile Ile Lys Arg Phe Glu Gln Lys Gly
            20                  25                  30

Phe Arg Leu Val Gly Leu Lys Phe Met Gln Ala Ser Glu Asp Leu Leu
        35                  40                  45

Lys Glu His Tyr Val Asp Leu Lys Asp Arg Pro Phe Phe Ala Gly Leu
    50                  55                  60

Val Lys Tyr Met His Ser Gly Pro Val Val Ala Met Val Trp Glu Gly
65                  70                  75                  80

Leu Asn Val Val Lys Thr Gly Arg Val Met Leu Gly Glu Thr Asn Pro
                85                  90                  95

Ala Asp Ser Lys Pro Gly Thr Ile Arg Gly Asp Phe Cys Ile Gln Val
            100                 105                 110

Gly Arg Asn Ile Ile His Gly Ser Asp Ser Val Glu Ser Ala Glu Lys
```

-continued

```
        115                 120                 125

Glu Ile Gly Leu Trp Phe His Pro Glu Glu Leu Val Asp Tyr Thr Ser
    130                 135                 140

Cys Ala Gln Asn Trp Ile Tyr Glu
145                 150


<210> SEQ ID NO 5
<211> LENGTH: 184
<212> TYPE: PRT
<213> ORGANISM: Homo Sapiens

<400> SEQUENCE: 5

Gly Gly Gly Glu Cys Cys Glu Pro Arg Gly Ser Arg Ala Arg Phe Gly
 1               5                  10                  15

Cys Trp Arg Leu Gln Pro Gln Phe Lys Pro Lys Gln Leu Glu Gly Thr
            20                  25                  30

Met Ala Asn Cys Glu Arg Thr Phe Ile Ala Ile Lys Pro Asp Gly Val
        35                  40                  45

Gln Arg Gly Leu Val Gly Glu Ile Ile Lys Arg Phe Glu Gln Lys Gly
    50                  55                  60

Phe Arg Leu Val Gly Leu Lys Phe Met Gln Ala Ser Glu Asp Leu Leu
65                  70                  75                  80

Lys Glu His Tyr Val Asp Leu Lys Asp Arg Pro Phe Phe Ala Gly Leu
                85                  90                  95

Val Lys Tyr Met His Ser Gly Pro Val Val Ala Met Val Trp Glu Gly
            100                 105                 110

Leu Asn Val Val Lys Thr Gly Arg Val Met Leu Gly Glu Thr Asn Pro
        115                 120                 125

Ala Asp Ser Lys Pro Gly Thr Ile Arg Gly Asp Phe Cys Ile Gln Val
    130                 135                 140

Gly Arg Asn Ile Ile His Gly Ser Asp Ser Val Glu Ser Ala Glu Lys
145                 150                 155                 160

Glu Ile Gly Leu Trp Phe His Pro Glu Glu Leu Val Asp Tyr Thr Ser
                165                 170                 175

Cys Ala Gln Asn Trp Ile Tyr Glu
            180


<210> SEQ ID NO 6
<211> LENGTH: 746
<212> TYPE: DNA
<213> ORGANISM: Homo Sapiens

<400> SEQUENCE: 6

ggcggggggg ggagtgctgc gaaccacgtg ggtcccgggc gcgtttcggg tgctggcggc     60

tgcagccgca gttcaaacct aagcagctgg aaggaaccat ggccaactgt gagcgtacct    120

tcattgcgat caaaccagat ggggtccagc ggggtcttgt gggagagatt atcaagcgtt    180

ttgagcagaa aggattccgc cttgttggtc tgaaattcat gcaagcttcc gaagatcttc    240

tcaaggaaca ctacgttgac ctgaaggacc gtccattctt tgccggcctg gtgaaataca    300

tgcactcagg gccggtagtt gccatggtct gggaggggct gaatgtggtg aagacgggcc    360

gagtcatgct cggggagacc aaccctgcag actccaagcc tgggaccatc cgtggagact    420

tctgcataca agttggcagg aacattatac atggcagtga ttctgtggag agtgcagaga    480

aggagatcgg cttgtggttt caccctgagg aactggtaga ttacacgagc tgtgctcaga    540

actggatcta tgaatgacag gagggcagac cacattgctt ttcacatcca tttcccctcc    600
```

-continued

```
ttcccatggg cagaggacca ggctgtagga aatctagtta tttacaggaa cttcatcata    660

atttggaggg aagctcttgg agctgtgagt tctccctgta cagtgttacc atccccgacc    720

atctgattaa aatgcttcct cccagc                                         746
```

PRODUCTION AND USE OF HUMAN NM23 PROTEIN AND ANTIBODIES THEREFOR

This application is a divisional of, and claims the benefit of, application Ser. No. 08/475,684, filed Jun. 7, 1995, which status is allowed, which is a divisional application Ser. No. 07/806,932, filed Dec. 11, 1991, which status is pending, which is a continuation-in-part of application Ser. No. 07/422,801, filed Oct. 18, 1989, which status is abandoned, which applications are hereby incorporated in their entirety herein by reference.

The present invention is a continuation-in-part of application Ser. No. 07/422,801 filed Oct. 18, 1989.

The present invention relates to human nm23 protein, DNA encoding human nm23 proteins, (or fragments or analogues of such DNA), antibodies which recognize human nm23 protein and processes and products for producing and using such materials.

Steeg et al., Journal of the National Cancer Institute 80:200–204, 1988 discloses a murine, nm23 gene, and corresponding protein which is associated with murine tumor metastatic potential.

Applicant has provided a human gene(s) encoding for a human nm23 protein(s), as well as the protein(s) and antibodies which car be used as an aid in predicting the aggressiveness of human tumors.

More specifically, the present invention relates to genetic testing for cancer susceptibility, diagnosis and prognosis. The present invention makes use of the marker of the nm23 genes, for which the human pnm23-H1 and pnm23-H2S and murine 23 and pnm23-1 recombinant cDNA clones have been described (3, 21–22). The genetic marker itself can be a whole gene, a fragment thereof, a genomic or cDNA clone, an adjacent region, or a regulatory region thereof. The purpose of this invention is to provide novel genetic methods for the detection of (a) susceptibility to cancer and (b) cancer tumorgenic and metastatic potential.

These methods are based on (a) structural and sequential evaluation of nm23 DNA and; (b) evaluation of novel nm23 expression patterns, either at the RNA, mRNA and/or protein levels. Such information is critical to the physician's selection of diagnostic and therapeutic regimens for the patient, both prior to the development of cancer and during cancer detection and treatment.

Therefore, in accordance with one aspect of the present invention, there is provided DNA, or a fragment, analogue or derivative of such DNA, which encodes a human nm23 protein.

In accordance with another aspect of the present invention, there is provided a cloning or expression vehicle which includes DNA, or a fragment, analogue or derivative of such DNA, which encodes a human nm23 protein.

In accordance with a further aspect of the present invention, there is provided a host; in particular cells, genetically engineered to include DNA, or a fragment or analogue or derivative of such DNA, which encodes a human nm23 protein or a fragment or analogue or derivative of of such DNA; i.e., such cells are modified to include human nm23 DNA.

In accordance with yet another aspect of the present invention, there is provided a human nm23 protein.

In accordance with yet a further aspect of the present invention, there is provided antibodies which recognize human nm23 protein.

In accordance with still a further aspect of the present invention, there is provided procedures for using the aforementioned DNA and antibodies for predicting the metastasic potential of tumors.

The term "human nm23 gene or DNA" as used herein means a gene or DNA which encodes a human nm23 protein, or an analogue or derivative or fragment of such DNA or gene which encompasses or includes a DNA sequence unique to DNA which encodes a human nm23 protein. Thus, the term human nm23 gene encompasses the genes or DNAs of Table 1 or fragments or derivatives or analogues of such genes.

"Human nm23 protein" means nm23 protein found in humans, or a fragment, analogue or derivative thereof which encompasses or includes an amino acid sequence which is unique to human nm23 protein and which preferably elicits an antibody which is recognized by human nm23 protein. The term human nm23 protein encompasses the proteins encoded by the genes of Table 1.

The term "antibody" as used herein encompasses polyclonal and monoclonal antibodies.

The term "nm23 antibody" means an antibody which is elicited in response to human nm23 protein or which recognizes human nm23 protein. An antibody which recognizes human nm23 protein may or may not be elicited in response to human nm23 protein.

Applicant has presently found two different and distinct human genes (DNA) which encode for two different and distinct nm23 proteins. The first gene is referred to herein as nm23-H1. The second gene is referred to herein as nm23-H2S. The gene sequences for both are shown in Table 1.

Although Applicant has presently identified two distinct human genes encoding for two different nm23 proteins, the scope of the present invention is not limited to such specific genes.

Human nm23 DNA (RNA) can be used as a diagnostic tool for detecting and/or determining RNA or DNA. For example, such DNA or RNA may be employed to detect mRNA expression in cancer cells to thereby aid in predicting the malignant potential of a human tumor. The methods which may be used include:

(1) RNA ("Northern") blotting. RNA can be isolated from tumor samples by any of a number of standard procedures. For example, refinements of the method of Lehrach (1) can be used. RNA is subjected to denaturing gel electrophoresis and transferred to nitrocellulose or other support matrix. The nm23 mRNA can be detected by hybridization of radioactively or non-radioactively labelled nm23-H1 or nm23-H2S. mRNA in the tumor will be reflected by the intensity of hybridization. For comparison, hybridization with control probes for mRNA whose level is constant (e.g. B-actin) allows normalization of results. Detection of low levels of nm23-H1 or nm23-H2S indicates a tumor of high malignant potential.

(2) Nuclease Protection assays. RNA isolated from tumor samples can be analyzed for the content of nm23-H1 or nm23-H2s by its ability for duplexes with a labelled complementary DNA or RNA. Using the whole or part of the nm23-H1 or nm23-H2S nucleotide sequence, plasmids can be generated for the production of nucleic acid probes complementary to the corresponding mRNA. Examples of such vectors are those based on the T7 or SP6 promoter for RNA probes or m13 phage for preparation of DNA probes using oligonucleotide priming. Probes prepared from such vectors will be allowed to hybridize to completion to RNA from tumor samples under conditions of excess of probe. Either RNase can be used to remove molar unhybridized RNA probes or S1 nuclease, or other single-stranded specific DNase, can be used to remove unhybridized DNA probe. These are then subject to denaturing gel electrophoresis and autoradiography. The intensity of bands corresponding to protected probe is a measure of the amount of either nm23-H1 or nm23-H2S from the sample. Inclusion of nuclease protection experiments for mRNAs whose levels do not change will allow normalization of results. Detection of tumors with relatively low levels of nm23-H1 or nm23-H2S indicates tumors of high malignant potential.

(2) In situ hybridization of nm23-H1 or nm23-H2S in tumor sections allow analysis of the quantity of nm23-H1 or H2S mRNA in individual cells of a tumor. Probe complementary to the nm23-H1 or H2S sequence can be prepared as described above and allowed to hybridize to mRNA within thin section of tumor sample (either embedded by standard techniques such as by the use of paraffin, or otherwise preserved). Unhybridized probe can be removed by nuclease. Hybridization can be detected by autoradiography or other methods. The intensity of hybridization reflects the amount of nm23-H1 or H2S mRNA within the cells of the tumor. When tumor cells contain low levels of nm23 they are likely to be highly malignant.

Susceptibility to early onset, familial breast cancer or other cancers could be detected by several methods, including analysis of the inheritance pattern of allelic fragments of a nm23 gene. Inheritance of an allele associated with the development of breast cancer in a patient's family would signify high risk for eventual cancer development. A second method to determine cancer susceptibility is to determine the DNA sequence of an nm23 gene, or its regulatory sequences, in DNA extracted from the patient's normal tissue. The presence of a mutation in the nm23 gene which would alter its amino acid sequence from the normal sequence would signify high risk of cancer development. Other mutations occuring in the regulatory DNA regions for nm23, or in intron regions responsible for normal processing and expression of these genes would also indicate high risk of cancer development.

Therefore, human nm23 DNA (RNA) may also be used to detect abnormalities of such DNA in normal or cancer cells to thereby aid in predicting the genetic predisposition for developing cancer or the aggressiveness of the cancer (abnormalities are found in more aggressive cells). Such methods include:

(1) DNA isolated from cells can be examined for abnormalities of the nm23-H1 or H2S gene by blot hybridization. DNA isolated from normal tissue and tumor tissue can be fragmented by restriction enzymes, subjected to gel electrophoresis transferred to nitrocellulose or other support matrix and the nm23-H1 and H2S genes' fragments detected by hybridization using probes containing all or part of the cDNAs described above or other regions of the nm23-H1 or H2S gene (Southern blot procedure). Differences in hybridization pattern between DNA from normal or tumor cells indicate abnormalities in the nm23-H1 or H2S gene.

(2) Identification of allele loss for the nm23-H1 or H2S genes. Restriction length polymorphisms (RFLP) for each nm23 gene can be identified by Southern blot procedure. An RFLP may be used to identify individual alleles for a gene in patients who are heterozygous for an RFLP. If DNA from normal and tumor cells from a single patient indicates that there is a an allelic loss in the tumor DNA for either nm23-H1 or H2S, such alteration indicates a tumor of high malignant potential.

Although the scope of the present invention is not intended to be limited to any theoretical reasoning, there are several theories which may explain the somatic allelic deletion of a metastasis-associated gene in primary tumors: (a) nm23-H1 may contribute to some aspects of the tumorigenesis process as well as metastasis. These theories are consistent with the experimental observations (19) that stable murine nm23-H1 transfected murine melanoma cells exhibited a reduced incidence of primary tumor formation; and (b) altered regulation of nm23-H1 may be an early event in the metastatic cascade, observable in primary tumor cells.

Additionally, Kerbel, et al. (20) have reported that occasional metastatic cells in a primary tumor have a selective growth advantage and at the later stages of primary tumor growth dominate the primary tumor. This "clonal dominance" of metastatic cells may contribute to the ability to detect nm23-H1 allelic deletions in certain primary tumor cells. Taken together the data identify nm23-H1 as a novel locus for allelic deletion in a variety of human carcinomas. The allelic deletion and homozygous deletion of nm23-H1 demonstrate that this gene shares a mechanism of altered regulation in cancer with known suppressor genes.

(3) Identification of genetic abnormalities within the gene sequence for the nm23-H1 or H2S. Nucleotide sequence analysis can be used to determined the gene structure of nm23-H1 or H2S in a tumor sample. The nucleotide sequence of nm23-H1 and H2S defines a normal sequence. Changes from these sequences in the DNA of patients indicates tumors of high metastatic potential or the predisposition to develop cancer.

The existence of point mutations can also be of prognostic utility in the determination of metastatic potential. The DNA sequence of a NM23 gene can be determined by standard methods such as cideoxy or Maxan-Gilbert sequencing and compared to the normal NM23 sequence. Alterations which would result in a change in amino acid sequence would be indicative of increased metastatic potential. Alterations in the sequence of chromosomal regulatory regions for the processing and expression of NM23 gene would also signify high metastatic potential.

Human nm23 DNA may be incorporated into a suitable expression vehicle to produce human nm23 protein.

The appropriate DNA sequence may be included in any of a wide variety of vectors or plasmids. Such vectors include chromosomal, nonchromosonal and synthetic DNA sequences; e.g., derivatives of SV40; bacterial plasmids; phage DNA's; yeast plasmids; vectors derived from combinations of plasmids and phage DNAs, viral DNA such as vaccinia, adenovirus, fowl pox, virus, pseudorabies, etc.

The appropriate DNA sequence may be inserted into the vector by a variety of procedures. In general, the DNA sequence is inserted into an appropriate restriction endonuclease site by procedures known in the art. Such procedures and others are deemed to be within the scope of those skilled in the art.

The DNA sequence in the vector is operatively linked to an appropriate expression control sequence(s) (promoter) to direct mRNA synthesis. As representative examples of such promoters, there may be mentioned: LTR or SV40 promoter, the *E.coli* lac or trp, the phage lambda PL promoter and other promoters known to control expression of genes in procaryotic and eukaryotic cells or their viruses. The expression vector also contains a ribosome binding site for translation initiation and a transcription terminator. The vector may also include appropriate sequences for amplifying expression.

In addition, the expression vectors preferably contain a gene to provide a phenotypic trait for selection of transformed host cells such as dihydrofolate reductase or neomycin resistance for eukaryotic cell culture, or such as tetracycline or ampicillin resistance in *E.coli.*

The vector containing the appropriate DNA sequence as hereinabove described, as well as an appropriate promoter or control sequence, may be employed to transform an appropriate host to permit the host to express the protein. As representative examples of appropriate hosts, there may be mentioned: bacterial cells, such as *E.coli, Salmonella typhimurium,* fungal cells, such as yeast; animal cells such as CHO or Bowes melanoma; plant cells, etc. The selection of an appropriate host is deemed to be within the scope of those skilled in the art from the teachings herein.

It is also possible to produce human nm23 protein by conventional peptide chemistry; e.g. by use of a peptide synthesizer and solid phase techniques.

Human nm23 protein can be employed to produce nm23 antibodies.

Antibodies against human nm23 protein may be produced by procedures generally known in the art. For example, polyclonal antibodies may be produced by injecting the protein alone or coupled to a suitable protein into a non-human animal. After an appropriate period, the animal is bled, sera recovered and purified by techniques known in the art. Monoclonal antibodies may be prepared, for example, by the Kohler-Millstein (2) technique involving fusion of an immune B-lymphocyte to myeloma cells. For example, antigen as described above can be injected into mice as described above until a polyclonal antibody response is detected in the mouse's sera. The mouse can be boosted again, its spleen removed and fusion with myeloma conducted according to a variety of methods. The individual surviving hybridoma cells are tested for the secretion of anti-nm23 antibodies first by their ability to bind the immunizing antigen and then by their ability to immunoprecipitate nm23-H1 and H2S from cells. Thus, the antibody elicited in response to human nm23 protein may be either a polyclonal or a monoclonal antibody.

nm23 antibodies can be used to detect tumors which have low levels of nm23 protein and thus an increased ability to metastasis or be malignant. Such antibodies may or may not be purified. The format for such assays include:

(1) Immunohistochemical analysis. Sections of the tumor can be reacted with anti-nm23-H1 or H2S antibodies and immunocomplexes detected by standard and commercial approaches such as peroxidase labelled second antibodies. The density of such immunostaining allows an estimation of the amount of nm23-H1 or H2S produced in the cell.

(2) Solid phase immunoassays. Such assays can be used to quantitatively determine the amount of nm23-H1 and H2S in a soluble extract of a tumor tissue. In such an assay one component either antibody or antigen is fixed to a solid support tumor.

Thus, in accordance with a further aspect of the present invention, there is provided an assay for detection or determination of human nm23 protein which employs nm23 antibody, of the type hereinabove described, as a specific binder in the assay.

The assay technique which is employed is preferably an assay wherein the nm23 antibody is supported on a solid support, as a binder, to bind human nm23 protein present in a sample, with the bound protein then being determined by use of an appropriate tracer.

The tracer is comprised of a ligand labeled with a detectable label. The ligand is one which is immunologically bound by the human nm23 protein and such ligand may be labeled by techniques known in the art.

Thus, for example, the human nm23 protein bound to the nm23 antibody on the solid support may be determined by the use of nm23 antibody which is labeled with an appropriate detectable label.

In such a sandwich assay technique, the labeled nm23 antibody may be a monoclonal antibody or a polyclonal antibody; e.g. the polyclonal antibody may be an antibody which is specific for human nm23 protein which antibody may be produced by procedures known in the art; for example innoculating an appropriate animal with human nm23 protein.

The detectable label may be any of a wide variety of detectable labels, including, enzymes, radioactive labels, chromogens (including both fluorescent and/or absorbing dyes) and the like. The selection of a detectable label is deemed to be within scope of those skilled in the art from teachings herein.

The solid support for the nm23 antibody may be any one of a wide variety of solid supports and the selection of a suitable support is deemed to be within the scope of those skilled in the art from the teachings herein. For example, the solid support may be a microtiter plate; a tube, a particle, etc.; however, the scope of the invention is not limited to any representative support. The nm23 antibody may be supported on the support by techniques known in the art; e.g., by coating; covalent coupling, etc. The selection of a suitable technique is deemed to be within the scope of those skilled in the art from the teachings herein.

The sandwich assay may be accomplished by various techniques; e.g., "forward"; reverse"; or "simultaneous"; however, the forward technique is preferred.

In a typical procedure, the nm23 antibody, which is supported on a solid support is initially contacted with a sample containing or suspected of containing human nm23 protein to bind specifically any of such protein present in the sample to such antibody on the support.

After washing of the solid support, the support is contacted with a tracer which binds to human nm23 protein. If such protein is present in the sample, the tracer becomes bound to such protein bound to the antibody on the solid support, and the presence of tracer on the solid support is indicative of the presence of human nm23 protein in the sample. The presence of tracer may be determined by determining the presence of the detectable label by procedures known in the art.

Although the preferred procedure is a sandwich assay, it is to be understood that the nm23 antibody may be used in other assay techniques, e.g., an agglutination assay wherein the nm23 antibody is used on a solid particle such as a latex particle.

In accordance with another aspect of the present invention, there is provided an assay kit or package for determining human nm23 protein which includes nm23 antibody, preferably nm23 antibody elicited in response to nm23 protein. The nm23 antibody may or may not be labeled with a detectable marker or label. If the kit is to be used for an immunohistochemical assay, the kit may include unlabeled nm23 antibody and a labeled antibody which immunobinds to the nm23 antibody. If the kit is to be used in an immunoassay, the kit may include both supported nm23 antibody and unsupported nm23 antibody which is preferably labeled with a detectable label or marker. The kit may also include other components, such as buffers etc.

The invention will be further described with respect to the following examples; however, the scope of the invention is not to be limited thereby. In the Examples, unless otherwise noted, purifications, digestions and ligations are accomplished as described in "Molecular Cloning, a laboratory manual" by Maniatis et al. Cold Spring Harbor Laboratory (1982).

EXAMPLE 1

Two distinct cDNAs were isolated form a cDNA library made form normal human fibroblast mRNA. Standard techniques were used throughout. As a probe, we used the 502 base HpaII restriction fragment of pnm23-M1. Steeg, et al. (3). This DNA was isolated from agarose gel electrophoretograms using DE45 membrane (Schlicher and Schuell). The DNA was made radioactive using the nick translation reaction (Amersham kit) and p32PdCTP (Amersham). The individual bacteria of the cDNA library, obtained from Hiroto Okayama, (Okayama, et al. (4)) was dispersed on agarose luria broth plates. Following growth they were transferred to nitrocellulose (Schlicher and Schuell), lysed using 0.5M NaOH and 1.5M NaCl, and neutralized in 1M NH Ac. DNA was fixed to the nitrocellulose by baking. Hybridization with the radioactive probe was conducted in 40% formamide, 0.75M NaCl, 0.075M Na citrate, 0.2% Bovine Serum Allbumen, 0.2% Ficol, and 0.2% polyvinyl pyrolidone, and 2 mg/ml DNA. Hybridization was conducted for 15 hours at 42° C. Following hybridization, the filter was washed twice with 0.3M NaCl, 0.03M Na citrate, at room temperature for 20 minutes followed by two wastes at 42° C. in 0.015M NaCl and 0.0015M Na citrate for 20 minutes each. Positive hybridization was detected for 5 bacterial by autoradiography. These were purified by single cell cloning.

DNA was extracted from each of the 5 clones and analyzed by restriction enzyme analysis. A distinct pattern was identified for two clones, pnm23-H1 and pnm23-H2. A second nm23-H2 cDNA clone was isolated from a human lung cDNA library using pnm23-H2 as a probe, the clone is termed nm23-H2S. The nm23-H1 and nm23-H2S clones were subjected to further analysis.

The DNA sequence of pnm23-H1 and pnm23-H2s was determined using the dideoxy chain termination method (5) (U.S. Biochemical kit). For this purpose, the cDNA of pnm23-H1 and pnm23-H2S were removed from the plasmid and inserted using standard techniques into the Sal I site of M13mp18 (BRL). DNA sequence analysis was conducted using synthetic 17 base oligonucleotides as reaction primers. The DNA sequence of pnm23-H1 and pnm23-H2S is shown in Table 1. Table 1 shows that pnm23-H1 contains nucleotide sequence upstream of the putative translation initiation codon (nucleotide 87). The non-identity of nucleotide sequence (94% similarity) indicates that pnm23-H1 and pnm23-H2S are the products of separate genes.

EXAMPLE 2

Production of nm23-H1 and nm23-H2S Protein

The nucleotide sequence of pnm23-H1 and H2S can be translated into a predicted protein sequence for the corresponding proteins. Several methods can be used to generate such protein.

(1) Standard chemical procedures can be used to synthesize peptides corresponding to all or a portion of the nm23-H1 or H2S amino acid sequence. These peptides can be coupled to carrier proteins such as KLH for antibody production.

(2) Protein corresponding to all or part of nm23-H1 or part of nm23-H2S can be synthesized in bacteria under the direction of bacterial transcription promotion signals. The nm23-H1 protein has been expressed under direction of the bacteriophage lambda PL promoter in a vector similar to others described (6). This vector was constructed as shown in FIG. 1. The plasmid pBR322 was digested with EcoRI and AvaI and the base fragment isolated by agarose gel electrophoresis. This was mixed with a synthetic restriction fragment (FIG. 1) containing several enzyme sites, a bacterial ribosome binding site and a translation initiation codon containing a NcoI restriction enzyme site. These were reacted with T4 DNA ligase transformed into *E.Coli* and plasmids of correct structure identified. DNA from these plasmids were digested with BstXI and BamHI and mixed with a BstXI-BglII digestion of the 4.5 kb Hind III fragment of bacteriophage DNA. This BstXI-BglII fragment contains the PL promoter. Following ligation and transformation into *E. Coli* (which contains a cI 857 prophage) plasmids containing the structure shown in FIG. 1 were identified. DNA from these plasmids was digested with BstXI and HpaI and the cohesive ends of each DNA filled in by *E. Coli* DNA polymerase I large fragment. This was ligated using standard conditions and transformed into *E. Coli* (7). The nm23-H1 was removed from M13mp18 by digesting with NcoI at a ratio of 1 unit of enzyme per 1 $\mu$g DNA for 2 minutes to produce partially digested molecules as verified by the conversion of supercoiled molecules to linear forms. This was phenol/$CHCl_3$ extracted and ethanol precipitated to remove NcoI enzyme and further digested with EcoRI. The 0.7 kb fragment was isolated from agarose gel electrophoretograms. This fragments were combined with plasmid pPL which had been digested with EcoRI and NcoI ligated and transformed into *E. Coli*.

Bacterial clones were identified which could direct the synthesis of human nm23-H1 protein. Bacteria were grown to OD 660=1 at 32° C. and temperature shifted to growth at 42° C. for 16 hours. Total bacterial protein was examined by electrophoresis in containing 15% polyacrylamide gels containing SDS. The human nm23-H1 protein was identified as a 19 kDa protein, capable of reacting with anti-peptide antisera directed against amino acids 86 to 102 of the protein.

The human nm23-H1 protein can be purified from the bacteria by a variety of methods. For example, following growth and temperature shift induction bacteria were lysed by sonication in 20 mM Tris pH 7.5 150 nM NaCl (TBS). Insoluble material was removed by centrifugation at 100,000×g for 30 minutes. Ammonium sulfate was then added to 40% saturated solution and proteins allowed to precipitate at 4° C. for 10 minutes. These proteins were removed by centrifugation at 100,000×g for 10 minutes. Solid ammonium sulfate was added to 60% saturated solution and proteins allowed to precipitate for 1 hr. at 4° C. These proteins were collected by centrifugation at 100,000×g and the precipitate dissolved in TBS. Following dialysis for 16 hours, a fine precipitate is collected by centrifugation at 10,000×g for 10 minutes. This is made soluble in TBS and 1 mM DTT. Protein prepared in this way is more than 80% pure as judged by SDS polyacrylamide gel electrophoresis. Protein prepared in this way is suitable for use as an immunizing antigen in antibody production and in biological modification experiments.

The nucleotide sequence of nm23-H1 and H2S allow the expression of either protein in eucaryotic cells. There are a variety of systems available for expression of proteins in cells ranging from yeast to human tissue culture cells. The essential elements required for expression of nm23-H1 or H2S protein was nucleotide sequences capable of directing synthesis of the nm23.

EXAMPLE 3

Production of nm23 Antibody

The products described in Example 3 section can be used as antigens. These can be used intact or following coupling to a carrier protein such as Keyhole Lympid Hemocyanin. Coupling can be conducted using established techniques and using such crosslinking agents as EDC. The antigen is then mixed with adjuvant (e.g., Freund's) and injected into the animal (such as rabbit, rat, or goat). Following booster injections with antigen mixed with adjuvant (e.g., Freunds incomplete) the animal is bled and sera prepared. The presence of antibody can be monitored by immunoprecipitation, western blot, or solid phase binding assay (e.g., ELISA). Polyclonal antisera to nm23-H1 or H2S can be prepared in purified form by affinity chromatography. The immunoglobulin molecules can be obtained from the sera by staphylococcal protein A binding and anti-nm23-H1 or H2S obtained by binding to a solid matrix to which the appopriate nm23 antigen has been chemically fixed.

EXAMPLE 4

Preparation of Monoclonal Antibody

Balb/c mice were made immune by 3 IP injections of 100 ug purified nm23-H1 protein of 1 week intervals mixed with Freund's complete adjuvant for the immunization and Freund's incomplete adjuvant for the boosters. Hybridomas were prepared by the method of Lane et al. *Methods in Enz.* 121, p. 183 (1986). The fusion partner was the myeloma P3×63 - Ag8.653 obtained from ATCC. Fused cells were plated with intraperitoneal cells obtained by the method of Lane, et al., *Hybridoma,* Vol. 7 p. 289 (1988). Hybridomas were grown in DMEM supplemented with NCTC-109 (Gibco) 7.5% Fetal Bovine Serum (Sigma) 7.5% CSPR-3 (Sigma) 1 mM Na pyruvate, 100 units Penicillin, 100 ug streptomycin, 10 ug/ml insulin, and 25 uM B-mercapto ethanol, containing 0.1 mM hypoxanthine, 0.4 uM amhopterin, and 0.016 mM Thymidine. Hybridoma clones were grown in 96 well dishes for two weeks. Anti-nm23 producing hybridomas were identified by ELISA. Purified nm 23-H1 protein was attached to Immulon 1 dishes and hybridoma culture media were allowed to react for 2 hours at room temperature. Antibody reaction was detected using biotinylated goat anti-mouse antibodies and steptavicdin horseradish peroxidase using the conditions in the BRL HyBRL kit. Positive hybridomas were cloned by limiting dilution in the above media containing 5% hybridoma growth supplement (Fisher). These were tested for reactivity in ELISA. This experiment has resulted in the isolation of two monoclonal antibodies identified as nmE302 and nm102B.

EXAMPLE 5

Detection of Metastatic Tumors

Antibodies specific for the human nm23-H1 and H2S proteins can be made as described. One such antibody directed against amino acids 45 to 61 of the nm23-H1 sequence was used to detect nm23 protein in tumor sections. Standard techniques can be used for the preparation of sections for immunohistochemistry. These methods include frozen sections or formalin fixation of the sample followed by paraffin embedding. In this example, tumor sections were fixed overnight in 10% neutral buffered formalin and embedded in paraffin using an automatic tissue processor (Fisher). Five micron sections were cut and deparaffinized using standard procedures involving xylenes and alcohol. Sections were then immunostained using affinity purified anti-peptide antibody at 1/200 diluttion: Immunostaining was done using standard techniques as provided by the manufacturer (Vector) using biotinylated goat antirabbit antibody followed by avidin biotinylated horse radish peroxidase. The color reaction (diamino benzidine tetrahydro chloride) at 0.5 mg/ml for 5 minutes at room temperature was followed by a water wash to stop reaction. Sections were then counter stained using Mayers hematoxylin, dehydrated and coverslips applied using standard methods. Sections were then examined by light microscopy for distinct cytoplasmic staining. Two samples from breast cancer patients where tumor had spread to the axillary lymph nodes show little staining; two samples from patients with cancer confined to the breast show distinct staining. This indicates that detection of low nm23 protein expression identifies malignant tumors with a propensity to spread outside the primary site.

The following is an example of a scoring system which has proved effective in the ability to score primary breast tumors as high or low level nm23 staining cells.

1) Examination of tumors using 10× objective and location of regions with the largest percentage of weakly staining cells.
2) Examination of the regions found in step 1 under high power (40× objective) and determination of the percentage of weakly staining cells, by counting the cells.

3) Evaluation of the percentage of weakly staining cells, should the percentage of weakly staining cells exceed 35% the tumor is considered to have low nm23 staining.

This scoring system has been used in distinguishing between a group of patients with low nm23 expression and a poorer overall survival rate and those patients with high nm23 expression and a higher overall survival rate. FIG. 2, is a graph depicting tumor cell percentage of nm23 staining vs estimated survival in years. In FIG. 2, A, B, and C, are determinations made by evaluations of the same data set by three independent pathologists. The dashed lines represent tumors expressing high NM23 expression the solid lines indicating low NM23 expression.

EXAMPLE 6

Somatic Cell Hybrid Analysis of Chromosal Localization

Somatic cell hybrid analysis of chromosamal localization. The isolation and characterization of the hybrids has been described (9–10). DNA samples from independent human-mouse and human-hamster somatic cell hybrids and subclones were digested with EcoRi, and the fragments resolved on 0.7% agarose gels. Southern blots were prepared on nylon membranes and hybridized to a random primer labeled 756 bp nm23-h1 cDNA insert (18). Blots were washed at high stringency (<10% divergence) in 0.1× SSC[3], 0.2% (w/v) SDS at 55° C. After autoradiography, the presence of the hybridizing human sequences in the DNA samples was correlated with the specific human chromosomes retained in each of the somatic cell hybrids.

The nm23-H1 gene was localized to human chromosome 17 by Southern blot analysis of DNA samples isolated from human-rodent somatic cell hybrids (Table 2). In EcoR1 digests the 21 kb and 4.6 kb (or 2.2 kb and 2.4 kb alleles) hybridizing human sequences segragated concordantly with chromosome 17 and discordantly (greater than 29%) with all other human chromosomes. A 1.7 kb human sequence segregated with chromosome 16 in these hybrids. In a second set of cell hybrids, in which human fiborblasts containing a 17;22 (p13;q11) reciprocal chromosome translocation were fused with Chinese hamster cells (9), the nm23-H1 gene segregated with the 17p12-qtr translocation chromosome and discordantly with the 17p13 band (data not shown). Thus, the nm23-H1 gene and the p53 tumor suppressor gene at 17p13 (10) were localized to different regions of chromosome 17.

EXAMPLE 7

In Situ Hybridization to Metaphse Chromosomes

Peripheral blood lymphocytes from a healthy male (46;XY) were cultured for 72 h at 37° C. in RPMI-1640 supplemented with 15% fetal bovine serum, phytohemagglutinin (0.5 μg/ml), and antibiotics.

Cultures were then synchronized by addition of BudR (100 ug/ml) for 16 h prior to washing and resuspension in fresh medium containing thymidine (2.5 ug/ml) and incubation for an additional 5.5 h (11) with Colcemid (0.05 ug/ml) present during the final 20 min. The cells were centrifuged, swollen, and fixed. Air dried metaphase spreads were prepared by standard procedures (12). After treatment with RNAse A (100 ug/ml) for 1 h at 37° C., the chromosomal DNA was denatured for 3 min in NaOH (0.07 N) in ethanol (64%) (13–14). Radiolabeled probe (specific activity $3.2\times10^7$ cpm/ug) was prepared by nick translation of the pNM23-H1 plasmid DNA with [$^3$H]dTTP and [$^3$H]dCTP. The probe was mixed with hybridization solution (formamide, 5% dextran sulphate, 2×Denhardt's solution, 2×SSC, 5 mM EDTA, 2 mM sodium phosphate (pH 6.4), and 200 ug/ml sheared herring sperm DNA), heat denatured, applied to slides ($3\times10^5$ cpm probe/slide), and hybridized for 20 h at 42° C. to remove the non specifically bound probe and coated with a 50% solution of NTB2 nuclear track emulsion (Kodak, Rochester, NY). The slides were stored dessicated at 4° C. for 9 days and then developed, stained (0.5% Wright's stan) and photographed. The slides were destained and chromosomal banding was obtained by staining with Hoechst 33258 (150 ug/ml) for 30 min and exposure to UV illumination for 30 min after rinsing. The slides were again stained with Wright's stain and the same metaphase spreads were rephotographed (120).

The nm23-H1 gene was further regionally localized to the centromeric region of chromosome 17 (p11-q11) by in situ hybridization to metaphase chromosomes (FIG. 3), and a cross hybridizing sequence on chromosome 16 was also observed (data not shown).

The functional nm23-H1 gene was definitely assigned to chromosome 17 by two different methods: first, a 200-base pair probe prepared from the 3' untranslated sequence from this cDNk identified the 21 kb EcoRI band which segregated with chromosome 17, and detected no sequences on chromosome 16 (data not shown); and second, using both EcoR1 and Bgl 11 polymorphisms for linkage analysis in the 40 C.E.P.H. pedigrees (15), a highly significant linkage was observed to the Hox-2 marker assigned to chromosome 17, which also suggested a regional localization to the proximal portion of the long arm, at 17q21. This is from a manuscript of STEEG's which is under preparation entitled: Chromosomal localization of Human NM23-H1 in the C.E.P.H. data base.

EXAMPLE 8

Allelic Deletion

Genomic DNA was isolated from the normal and tumor tissues of 109 cancer patients by standard methods. DNA was restricted with Bgl II, resolved on 0.8% agarose gels, and Southern blots were prepared. Southern blots were hybridized to a random primer labeled 756-base pair pNM23-H1 insert (18) in 50% (v/v) formamide, 5×SSC, 50 mM Tris-HCI, (pH/7.5), 5×Denhardt's solution, 0.5% (w/v) SDS, 250 ug/ml denatured salmon sperm DNA, 0.1% (w/v) dextran sulfate at 42° C., washed to a final stringency of 0.1×SSC, 0.2% (w/v) SDS-1, mM EDTA, 65° C.; and hybridization detected by autoradiography.

A Bgl II restriction fragment length polymorphism (RFLP) of human chromosomal DNA, which identified nm23-H1 allelic bands at 2.3 kb and 7.6 kb, was used for analysis of possible nm23-H1 somatic allelic deletion in human carcinomas. A total of 109 paired DNA samples from matched normal tissue and renal, lung, colon or breast carcinomas were analyzed for possible nm23-H1 allelic deletions (FIGS. 4–5). In human breast carcinomas, 64% of informative (heterozygous) tumors exhibited a deletion of one nm23-H1 allele (FIG. 4A). Previous studies with this same cohort of breast tumors analyzed allelic deletion at the transforming growth factors (2p13), somatostatin (3p28), MYB (6q22–23) and platelet derived growth factor (22q12.3-q13.1) loci, and reported a background rate of allelic deletion of less than 7% (16). In non-small cell lung carcinomas, 42% of informative cases exhibited nm23-H1 allelic (FIG. 4B). All of the lung tumors exhibiting nm23-H1 allelic deletions were adenocarcinomas; tumors without detectable nm23-H1 allelic deletion included adenocarcinomas, osteosarcomas, squamous cell carcinomas and large cell carcinomas. These data stand in contrast to previous studies in non-small cell lung carcinomas, in which allelic deletions at other chromosome 17 loci were observed primarily in squamous cell carinomas (17). Among renal carcinomas from patients were metastatic disease, 20% of informative cases exhibited nm23-H1 allelic deletion (FIG. 4C). A cell line established from each tumor to eliminate normal cell contamination indicated that the small amount of remaining nm23-H1 hybridization to tumor DNA was due to the presence of contaminating normal cells. Finally, among invasive (Duke's C classification) colon carcinomas, 22% of informative cases exhibited nm23-H1 allelic deletions (FIG. 5A, normal and tumor lanes). The data establish that the nm23-H1 gene is subject to somatic allelic deletion in human tumors.

In the colon carcinoma case shown in FIG. 3A, DNA samples from normal colonic mucosa, the primary tumor and a lymph node metatasis were examined. In addition to the allelic deletion in the primary tumor, previously described, a homozygous deletion of nm23-H1 was observed in the lymph node metastasis. Rehybridization of the same filter with a control Ha-ras probe (11p15.5) indicated approximately equivalent amounts of DNA in each lane (FIG. 5B). on a long exposure, a small amount of hybridization to the nm23-H1 bands was observable in the lymph node metastasis DNA, but may result from contaminating normal cells, as was demonstrated in renal carcinoma. The data in this case indicate a sequential series of alterations, from a single allelic deletion to a homozygous deletion, that was correlated with metastatic progression. The normal, primary tumor and lymph node metastasis DNAs from this patient each exhibited bands of hybridization to the p53 suppressor gene on Southern blots, but the case was uninformative for allelic deletion at this locus (data now shown). Thus, the nm23-H1 homozygous deletion data were not due to the complete deletion of both copies of chromosome 17.

The relative independence of nm23-H1 allelic deletions to allelic deletions at other chromosome 17 loci was determined. The normal/tumor DNA sets were hybridized to at least three other chromosome 17 probes, including p53, (17p13, Bgl II digest); YNZ22.1, (17p13.3, BamH1, Taq1 or Hin fl digests); p144D6 (17p13.3, Pstl digest); pHF 12.2 (17p12, Mspl digest); THH59 (17q23–25.3, Pvull digest). Nine normal/tumor DNA sets were identified that: (a) were informative for both nm23-H1 and another chromosome 17 probe, and (b) exhibited a nm23-H1 allelic deletion. Of these, 2 cases exhibited an nm23-H1 allelic deletion, but were heterozygous at the YNZ22.1 locus; One case exhibited an nm23-H1 allelic deletion, but was heterozygous at the p53 locus. the data indicate that deletions of relatively large areas of chromosome 17 occur in many tumors, suggesting that nm23-H1 and/or other chromosome 17 genes may be the targets; in 3/9 cases, however, evidence for specificity in nm23-H1 allelic deletion was obtained.

Numerous modifications and variations of the present invention are possible in light of the above teachings; therefore, within the scope of the appended claims, the invention may be practised otherwise than as particularly described.

```
nm23-H2S                                      CGG CCA CGA GGC GGA ATC CCT TCT GCT CTC CCA GCG CAG CGC CGC CGC CCG GCC CCT CCA GCT    63
                                              Arg Pro Arg Gly Gly Ile Pro Ser Ala Leu Pro Ala Gln Arg Arg Arg Pro Ala Pro Pro Ala
                                               :
             Gly Gly Gly Glu Cys Cys Glu Pro Arg Gly Ser Arg Ala Arg Phe Gly Cys Trp Arg Leu Gln Pro Gln Phe Lys Pro Lys Gln Leu
nm23-H1     GG CGG GGG GGG GAG TGC TGC GAA CCA CGT GGG TCC CGG GCG CGT TTC GGG TGC TGG CGG CTG CAG CCG CAG TTC AAA CCT AAG CAG CTG   89

   H2S    TCC CGG ACC ATG GCC AAC CTG GAG CGC ACC TTC ATC GCC ATC AAG CCG GAC GGC GTG CAG CGC GGC CTG GTG GGC GAG ATC ATC AAG CGC    153
          Ser Arg Thr Met Ala Asn Leu Glu Arg Thr Phe Ile Ala Ile Lys Pro Asp Gly Val Gln Arg Gly Leu Val Gly Glu Ile Ile Lys Arg
                   :   :   :   :       :   :   :   :   :   :   :   :   :   :   :   :   :   :   :   :   :   :   :   :   :   :   :
          Glu Gly Thr Met Ala Asn Cys Glu Arg Thr Phe Ile Ala Ile Lys Pro Asp Gly Val Gln Arg Gly Leu Val Gly Glu Ile Ile Lys Arg
   H1     GAA GGA ACC ATG GCC AAC TGT GAG CGT ACC TTC ATT GCG ATC AAA CCA GAT GGG GTC CAG CGG GGT CTT GTG GGA GAG ATT ATC AAG CGT    179

   H2S    TTC GAG CAG AAG GGA TTC CGC CTC GTG GCC ATG AAG TTC CTC CGG GCC TCT GAA GAA CAC CTG AAG CAG CAC TAC ATT GAC CTG AAA GAC    243
          Phe Glu Gln Lys Gly Phe Arg Leu Val Ala Met Lys Phe Leu Arg Ala Ser Glu Glu His Leu Lys Gln His Tyr Ile Asp Leu Lys Asp
           :   :   :   :   :   :   :   :   :           :   :           :   :   :           :   :           :           :   :   :
          Phe Glu Gln Lys Gly Phe Arg Leu Val Gly Leu Lys Phe Met Gln Ala Ser Glu Asp Leu Leu Lys Glu His Tyr Val Asp Leu Lys Asp
   H1     TTT GAG CAG AAA GGA TTC CGC CTT GTT GGT CTG AAA TTC ATG CAA GCT TCC GAA GAT CTT CTC AAG GAA CAC TAC GTT GAC CTG AAG GAC    269

   H2S    CGA CCA TTC TTC CCT GGG CTG GTG AAG TAC ATG AAC TCA GGG CCG GTT GTG GCC ATG GTC TGG GAG GGG CTG AAC GTG GTG AAG ACA GGC    333
          Arg Pro Phe Phe Pro Gly Leu Val Lys Tyr Met Asn Ser Gly Pro Val Val Ala Met Val Trp Glu Gly Leu Asn Val Val Lys Thr Gly
           :   :   :   :       :   :   :   :   :   :       :   :   :   :   :   :   :   :   :   :   :   :   :   :   :   :   :   :
          Arg Pro Phe Phe Ala Gly Leu Val Lys Tyr Met His Ser Gly Pro Val Val Ala Met Val Trp Glu Gly Leu Asn Val Val Lys Thr Gly
   H1     CGT CCA TTC TTT GCC GGC CTG GTG AAA TAC ATG CAC TCA GGG CCG GTA GTT GCC ATG GTC TGG GAG GGG CTG AAT GTG GTG AAG ACG GGC    359

   H2S    CGA GTG ATG CTT GGG GAG ACC AAT CCA GCA GAT TCA AAG CCA GGC ACC ATT CGT GGG GAC TTC TGC ATT CAG GTT GGC AGG AAC ATC ATT    423
          Arg Val Met Leu Gly Glu Thr Asn Pro Ala Asp Ser Lys Pro Gly Thr Ile Arg Gly Asp Phe Cys Ile Gln Val Gly Arg Asn Ile Ile
           :   :   :   :   :   :   :   :   :   :   :   :   :   :   :   :   :   :   :   :   :   :   :   :   :   :   :   :   :   :
          Arg Val Met Leu Gly Glu Thr Asn Pro Ala Asp Ser Lys Pro Gly Thr Ile Arg Gly Asp Phe Cys Ile Gln Val Gly Arg Asn Ile Ile
   H1     CGA GTC ATG CTC GGG GAG ACC AAC CCT GCA GAC TCC AAG CCT GGG ACC ATC CGT GGA GAC TTC TGC ATA CAA GTT GGC AGG AAC ATT ATA    449

   H2S    CAT GGC AGT GAT TCA GTA AAA AGT GCT GAA AAA GAA ATC AGC CTA TGG TTT AAG CCT GAA GAA CTG GTT GAC TAC AAG TCT TGT GCT CAT    513
          His Gly Ser Asp Ser Val Lys Ser Ala Glu Lys Glu Ile Ser Leu Trp Phe Lys Pro Glu Glu Leu Val Asp Tyr Lys Ser Cys Ala His
           :   :   :   :   :   :       :   :   :   :   :   :       :   :   :       :   :   :   :   :   :   :       :   :   :
          His Gly Ser Asp Ser Val Glu Ser Ala Glu Lys Glu Ile Gly Leu Trp Phe His Pro Glu Glu Leu Val Asp Tyr Thr Ser Cys Ala Gln
   H1     CAT GGC AGT GAT TCT GTG GAG AGT GCA GAG AAG GAG ATC GGC TTG TGG TTT CAC CCT GAG GAA CTG GTA GAT TAC ACG AGC TGT GCT CAG    539

   H2S    GAC TGG GTC TAT GAA TAA GAGGTGG---------------------ACACAACAGCAGTCTCCTTCAGCACGGCGTGGTGTGTCCCTGGACACAGCTCTTCATTCCAT       600
          Asp Trp Val Tyr Glu TER
               :       :   :
          Asn Trp Ile Tyr Glu TER
   H1     AAC TGG ATC TAT GAA TGA CAGGAGGGCAGACCACATTGCTTTTCACATCCATTTCCCCTCCTTCCCATGGGCAGAGGACC--------------------------------  619

   H2S    TGACTTAGAGGCAACAGGATTGATCATTCTTTTATAGAG------CATATTTGCCAATAAAGCTTTTGGAAGCCGG    Poly A                             670
   H1     --------AGGCTGTAGGAAATCTAGTTATTTACAGGAACTTCATCATAATTTGGAGGGAAGCTCTTGGAGCTGTGAGTTCTCCCTGTACAGTGTTACCATCCCCGACCA          721

   HI     TCTGATTAAAATGCTTCCTCCCAGC    Poly A                                                                                      746
```

TABLE 2

Segregation of nm23-H1 gene with human chromosome 17

| Human | Gene/Chromosome | | | | & |
|---|---|---|---|---|---|
| Chromosome | +/+ | +/− | −/+ | −/− | Discordancy |
| 1 | 28 | 26 | 3 | 35 | 32 |
| 2 | 24 | 30 | 2 | 36 | 35 |
| 3 | 22 | 32 | 13 | 25 | 49 |
| 4 | 38 | 16 | 20 | 18 | 39 |
| 5 | 19 | 35 | 6 | 32 | 45 |
| 6 | 31 | 23 | 16 | 22 | 42 |
| 7 | 29 | 25 | 8 | 30 | 36 |
| 8 | 27 | 27 | 9 | 29 | 39 |
| 9 | 23 | 31 | 9 | 29 | 43 |
| 10 | 15 | 39 | 4 | 34 | 47 |
| 11 | 23 | 31 | 4 | 34 | 38 |
| 12 | 31 | 23 | 6 | 32 | 32 |
| 13 | 30 | 24 | 3 | 35 | 29 |
| 14 | 31 | 23 | 10 | 28 | 36 |
| 15 | 30 | 24 | 15 | 23 | 42 |
| 16 | 27 | 27 | 10 | 28 | 40 |
| 17 | 54 | 0 | 0 | 38 | 0 |
| 18 | 35 | 19 | 13 | 25 | 35 |
| 19 | 23 | 31 | 5 | 33 | 39 |
| 20 | 29 | 25 | 11 | 27 | 39 |
| 21 | 37 | 17 | 23 | 15 | 43 |
| 22 | 17 | 37 | 9 | 29 | 50 |
| X | 29 | 25 | 18 | 20 | 47 |

A=Ava I; R=Eco RI; B=BamH I; Bx=Bst XI; H=HpaI; N=NcoI

The Bacteriophage Lambda PL promoter location is indicated by an arrow and "PL". The Lambda bacteriophage lambda N gene is indicated by a box and "N gene". The position of a ribosome binding sequence is indicated by S/O. The position of the protein initiator atg is indicated by "atg". Where two arrows converge where a ligation reaction is performed.

FIG. 2 Legend

Differential survival of patients with different levels of nm23 expression. A, B, C represent scoring of 44 patients nm23 levels by immunohistochemistry as described. A, B and C are results obtained by three independent pathologists. The dotted lines are high nm23 expressing patients solid lines are low=nm23 expressing patients. The plotting method is of Kaplan and Meyer (8).

Table 1 Legend

The nucleotide and predicted amino acid sequences of nm23-H1 and nm23-H2S cDNA clones SEQ ID NOS: 1–6. The asterisk marks the extent an initial incomplete nm23-H2 cDNA clone used to isolate the complete nm23-H2S cDNA clone.

Figure 1:
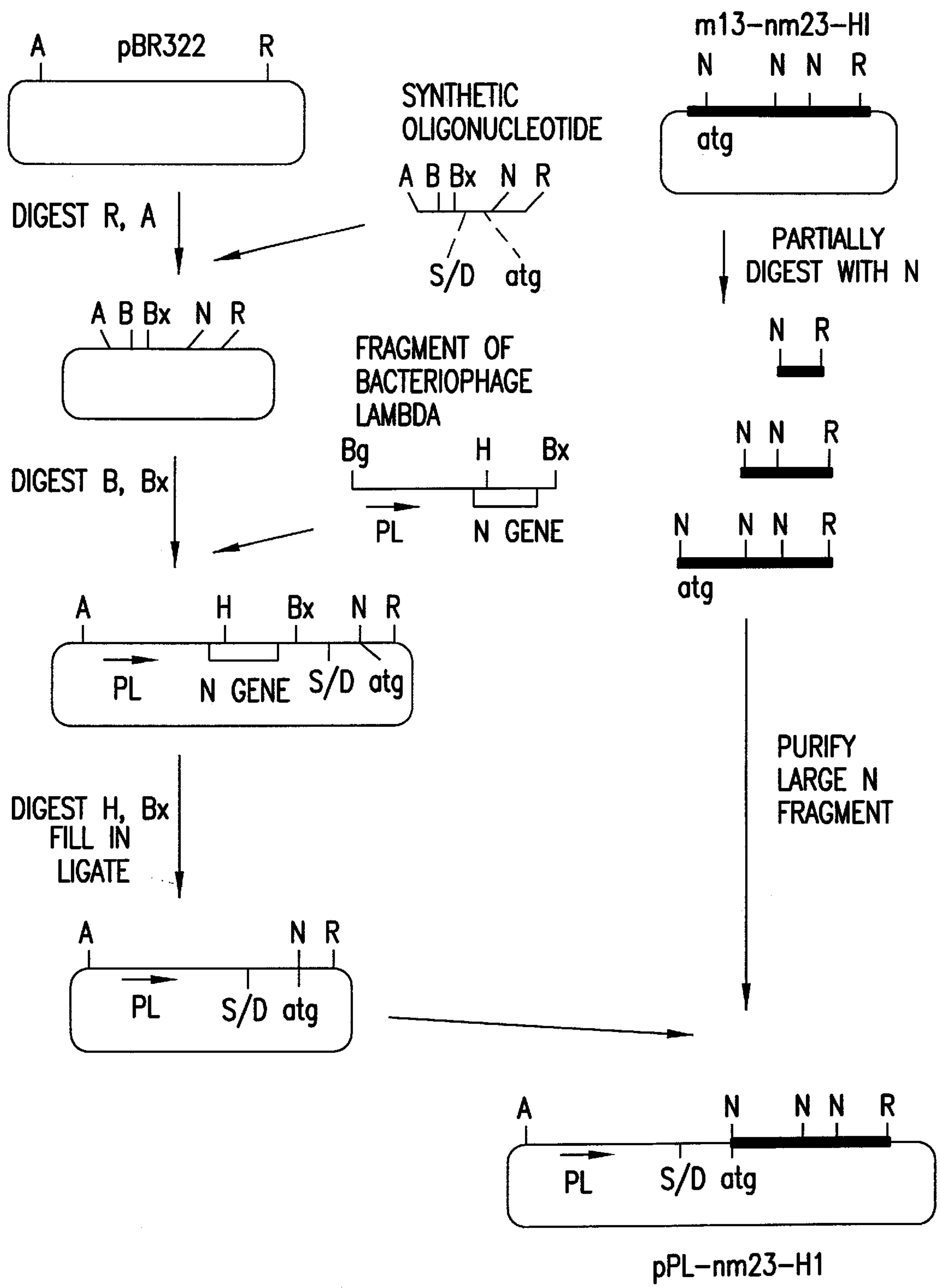
FIG. 1 Legend
Figure 2A:
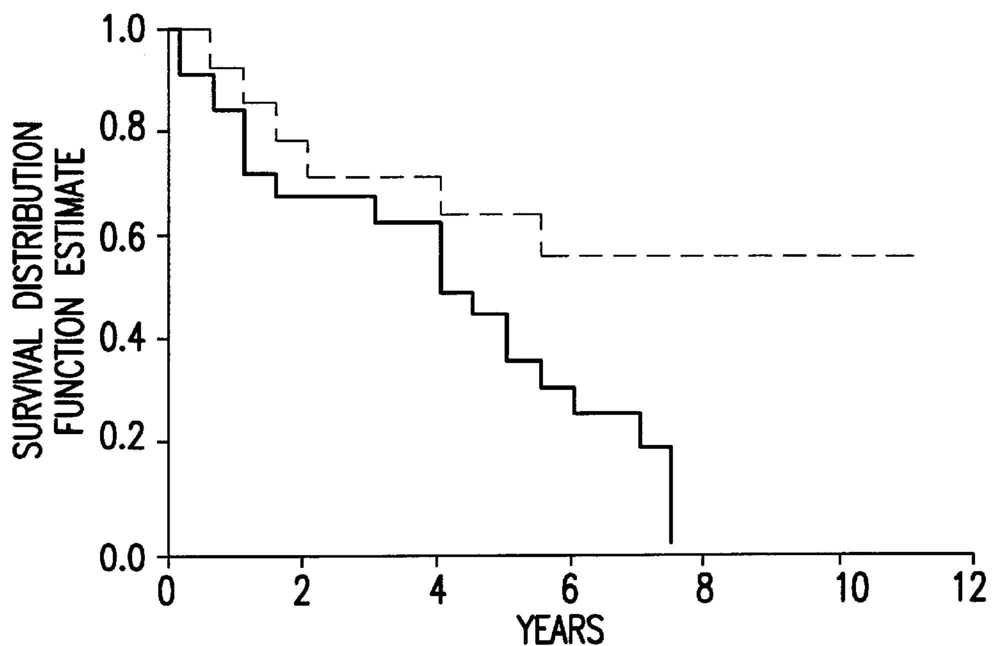
Figure 2B:
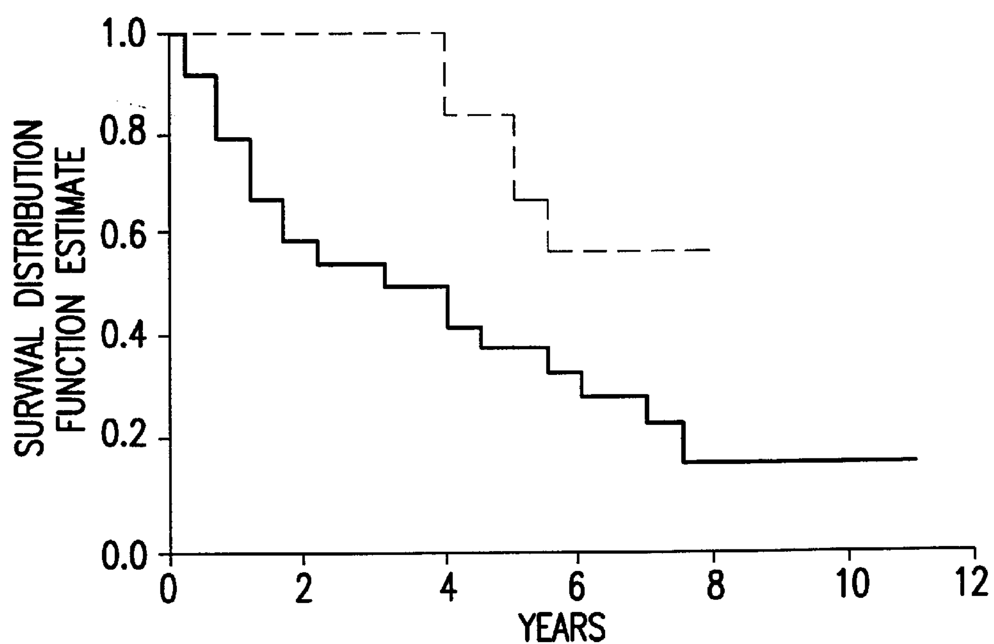
Figure 2C:
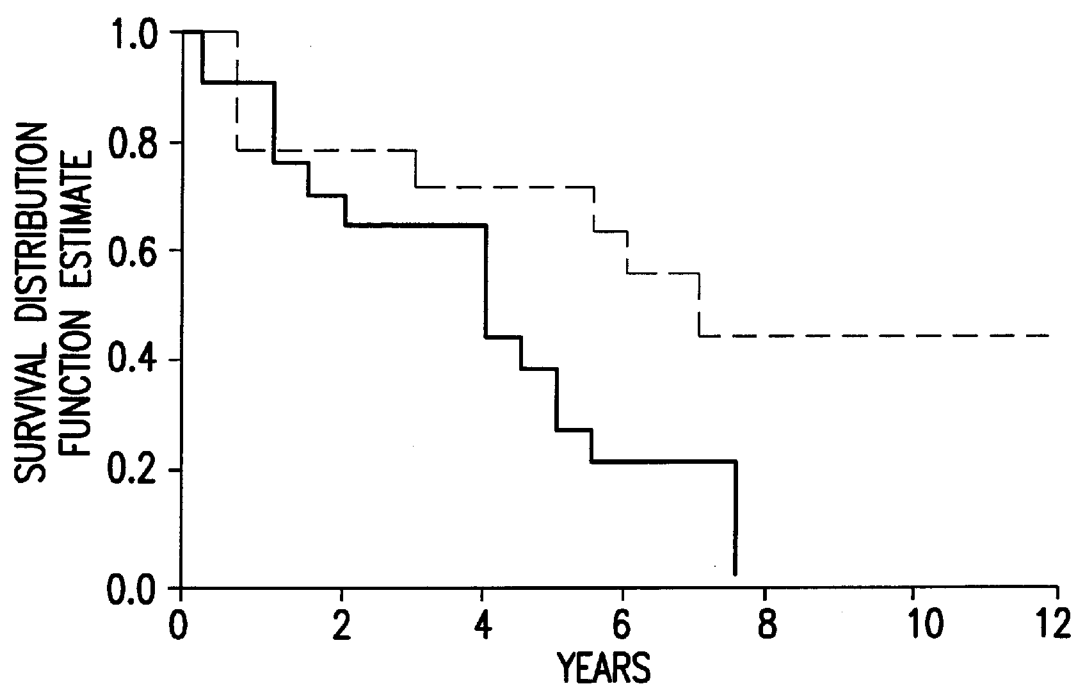
Figure 3A:
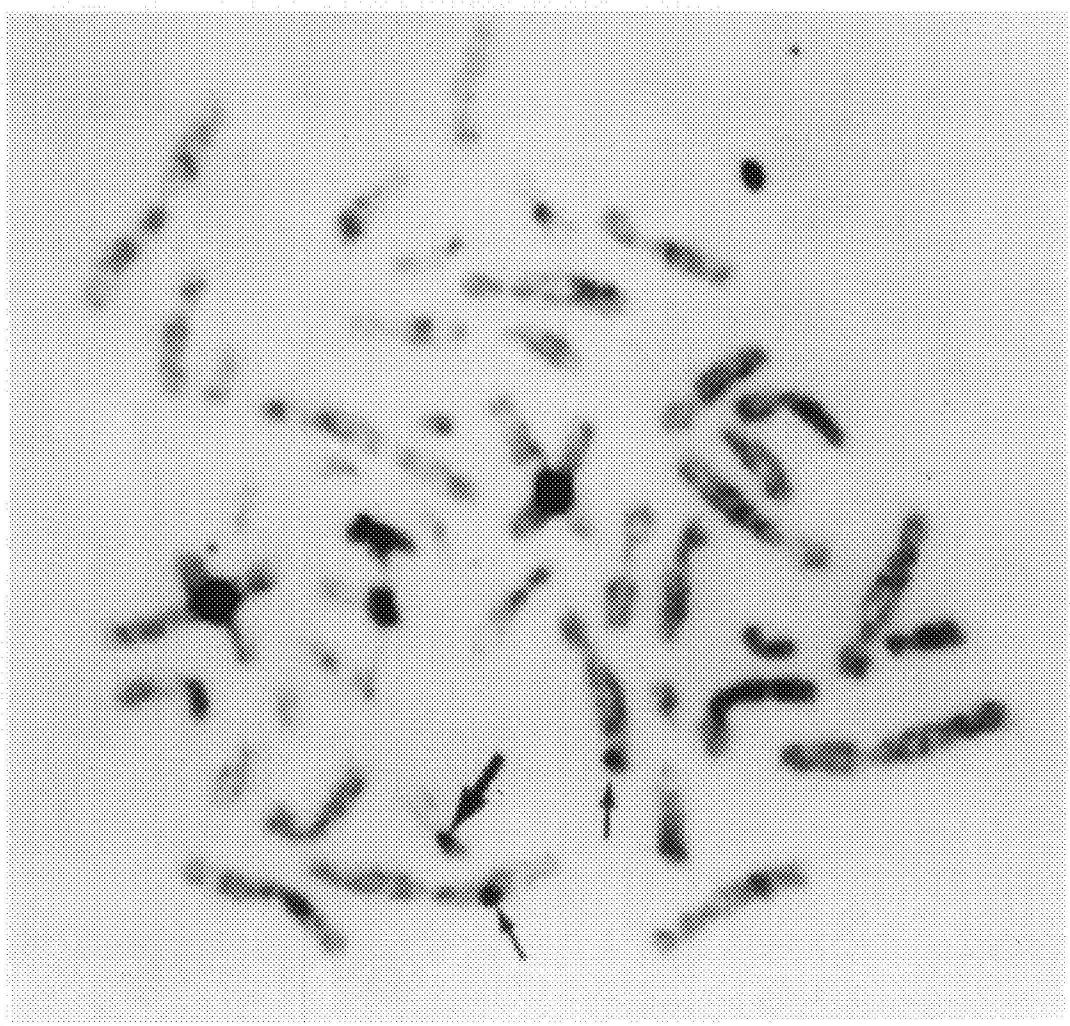
Figure 3B:
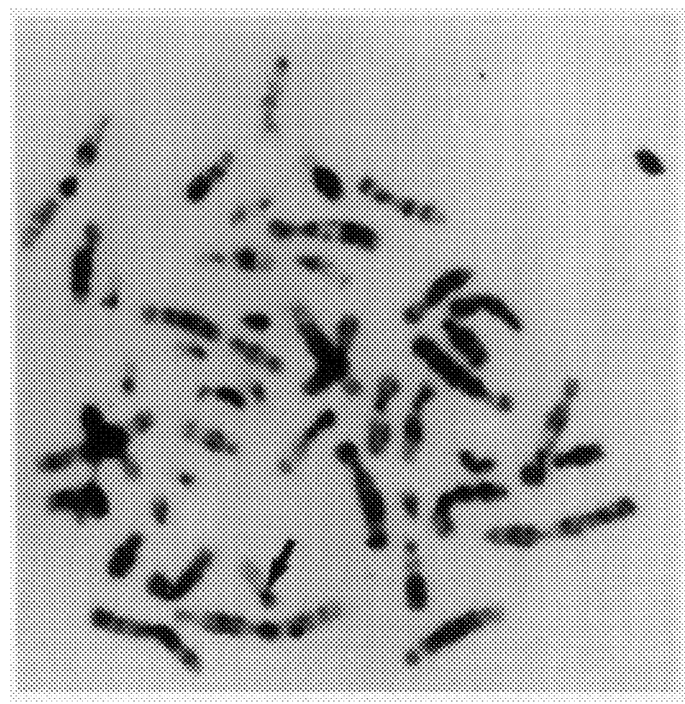
Figure 3C:
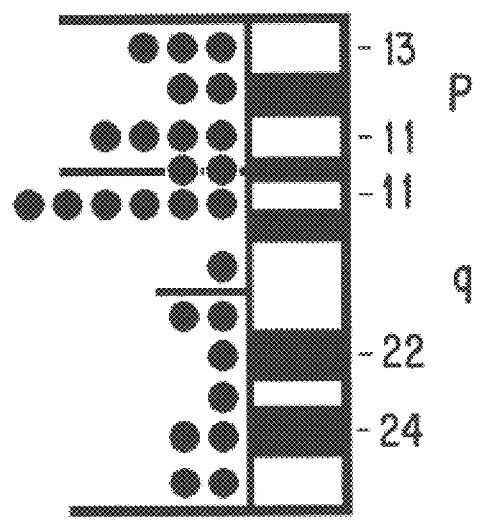

FIG. 3. In situ hybridization of pnm23-H1 to metaphse chromosomes. Panel A. Metaphase spread containing a grain on chromosome 17 (broad arrow). Two small arrows identify nonspecific hybridization. Panel B. The same metaphase spread as shown in A after chromosome banding. Panel C. Distribution of grains on chromosome 17 in 61 metaphase spreads. Twenty-six (17.8%) of 146 total grains were present on chromosome 17 and twelve (46%) of these 26 grains were localized to the 17p11-q11 region.

Figure 4A:
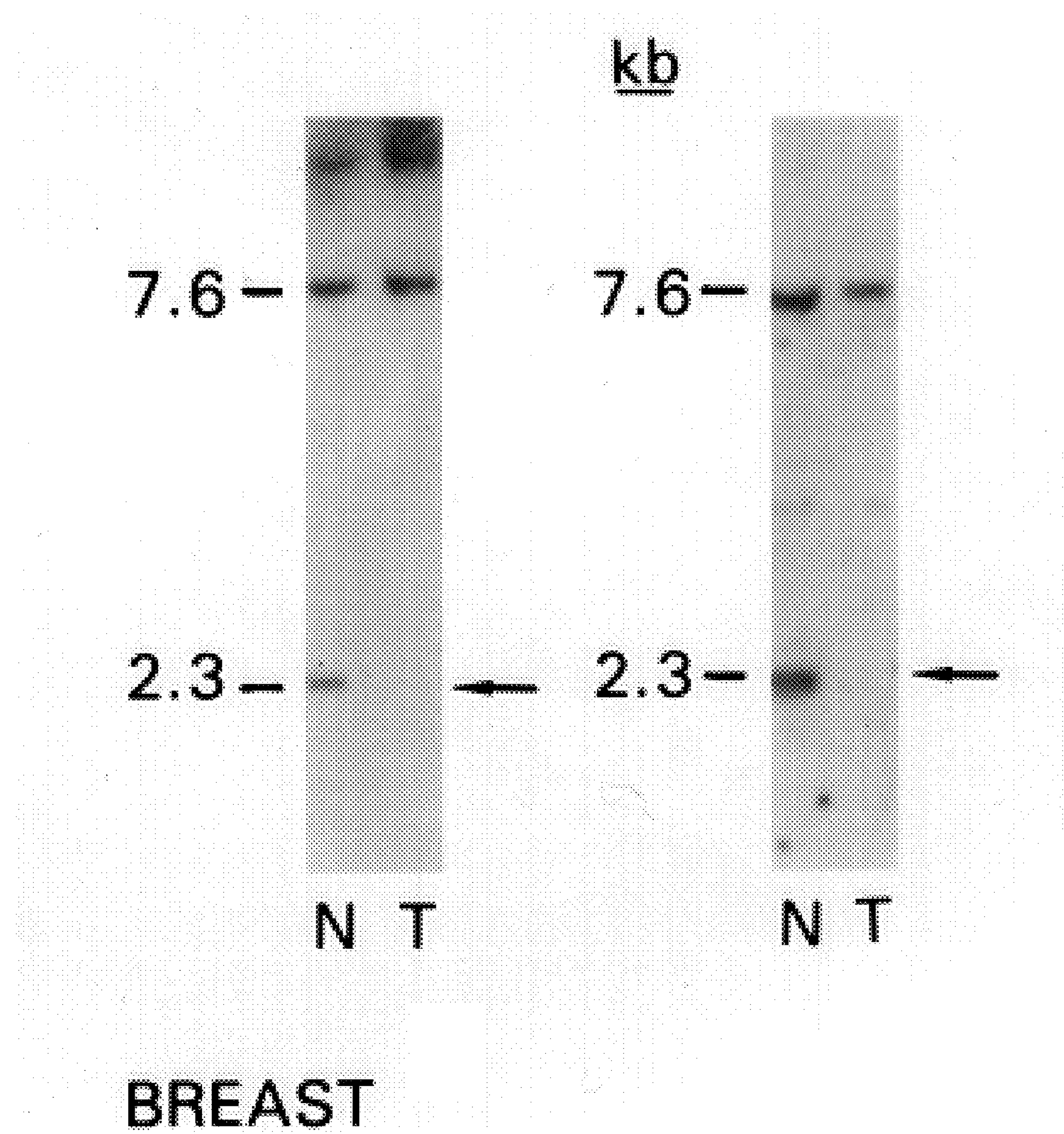
Figure 4B:
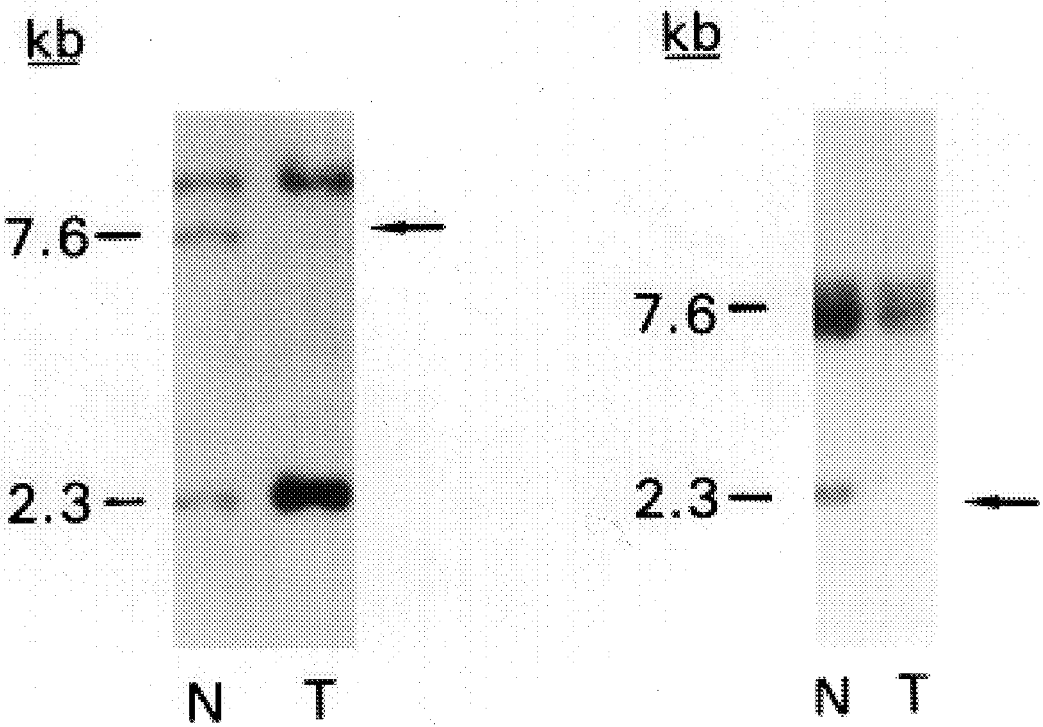
Figure 4C:
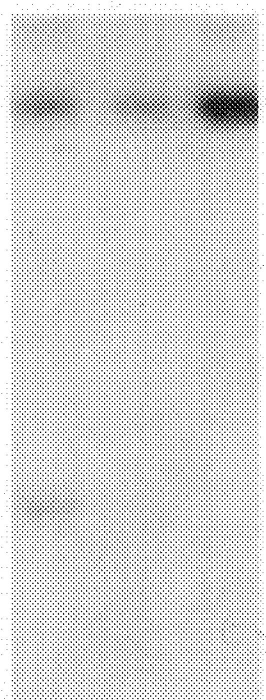

FIG. 4. Allelic deletion of nm23-H1 in tumors. Southern hybridization to BgIII digested human chromosomal DNA samples from: A, normal lymphocyte and breast carcinoma. B, normal lung and non-small cell ung carcinoma. C, normal kidney, kidney carcinoma and kidney carcinoma cell line. The BgIII restriction digest identified two allelic bands at 7.6 and 2.3 kb. A non allelic 21 kb constant bank was also evident. N: normal; T: tumor; C: tumor cell line. Numbers on the left on each panel indicate the size of the allelic banks. Arrows on the right indicate missing allele.

Figure 5:
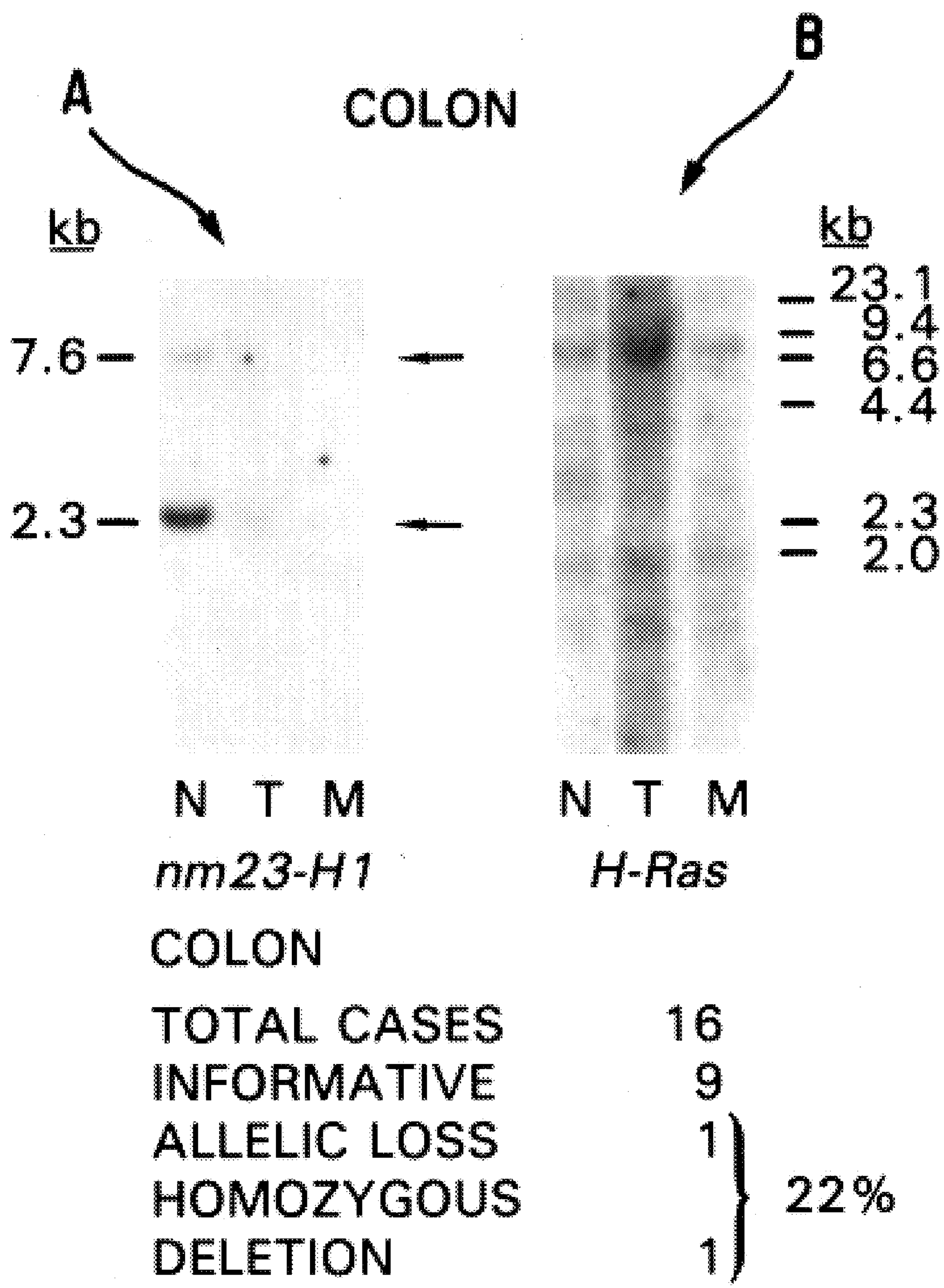

FIG. 5. Homozygous deletion of nm23-H1 in colon carcinoma metastasis. A. Southern hybridization of chromosomal DNA from normal colonic mucosa (N), colon carcinoma (T) and lymph node metastasis (M) to nm23-H1. B. Control southern hybridization of the same filter to human Ha-ras. The probate to Ha-ras, which maps to chromosome 11p15.5, was a 6.6 Kb insert spanning the entire genomic sequence.

Table 2. Southern blots of human roden somatic cell hybrid DNA samples were hybridized to a 756 bp fragment of the pnm23-H1 clone. A 4.6 kb nm23-H1 band was allelic with 2.2 and 2.4 kb banks. A 21 kb non allelic nm23-H1 bank was also detected. These banks were readily resolved from 3.2 kb, 5.1 kb, 6.1 kb, 6.9 kb, and 7.9 kb bands or 1.3 kb, 3.5 kb, 4.3 kb, 4.9 kb, and 5.8 kb cross-hybridizing bands in Chinese hamster and mouse digests, respectively. Detection of the human bands was correlated with the presence or absence of each human chromosome in the group of somatic cell hybrids. Discordancy represents presence of the gene in the absence of the chromosome (+/−) or absence of the gene despite the presence of the chromosome (−/+), and the sum of these numbers divided by total hybrids examined (×100) represents percent discordancy. The human-hamster hybrids contained 27 primary clones and 13 subclones (16 positive of 40 total) and the human-mouse hybrids represented 16 primary clones and 36 subclones (38 positive of 52 total).

REFERENCES

1. Lehrach, H, *Biochemistry* 16, p. 4743 (1975).

2. Kohler-Millstein, Galfre, G., and Milstein, C., *Methods Enz.* 73 p. 1 (1981).

3. Steeg et al., *JNCI* 80 p. 200 (1988).

4. Okayama, H, and Berg, P, *Mol. Cell Biol.* 3, p. 280 (1983).

5. Sanger, F., et al. *Proc. Nat'l Acad. Sci., USA* 74, p. 5463 (1977).

6. Rosenberg, M. and Shatzman A. *Methods Enz.* 101, p. 123 (1983).

7. Transformation into *E. Coli,* Maniatis, T., et al. *Molecular Cloning,* Cold Spring Harbor Laboratory (1982).

8. Kaplan, E. L., Meyer, P., Journal of the American Statistics Assoc. 53:457–481 (1958).

9. Mcbride, O. W., et al., Proc. Natl. Acad. Sci. USA 83:130–134 (1986).

10. Mcbride, O. W., et al., Nucleic Acids Res. 11:8221–8236 (1982).

11. Bhatt, B., et al., Nucleic Acids Res. 16:3951–3961 (1988).

12. Harper, M., et al., Chromosoma (Berl.) 83:431–439 (1981).

13. Singh, I., et al., Chromosoma (Berl.) 60:377–389 (1977).

14. Landegent, J. E., et al., Nature (London) 317:175–177 (1985).

15. Dausset, J., Genomics 6:575–577 (1990).

16. Cropp, C. S., et al., Proc. Natl. Acad. Sci. USA 87:7737–7441 (1990).

17. Weston, A., et al., Proc. Natl. Acad. Sci USA 86:5099–5103 (1989).

18. Rosengard, A. M., et al., Nature (London) 342:177–180 (1989).

19. Leone, A., et al., Reduced tumor incidence, metastatic potential and cytokine responsive of nm23 transfected melanoma cells, Cell in press 1991.

20. Kerbel, R. S., et al., Cancer Surv. 7:597–629 (1988).

21. Steeg, P. S., et al., Cancer Res. 48:6550–6554 (1988).

22. Steeg, P. S., et al., Cancer Metastasis (eds. Schirrmacher, V. and Schwartz-Albiez, R.) 48–52 (Springer, Heidelberg 1989).

What is claimed is:

1. Human nm23 protein.

2. Human nm23 protein of claim 1 having the sequence designated as NM23-H1 of Table 1.

3. Human nm23 protein of claim 1 having the sequence designated as NM23-H2S of Table 1.

4. The protein of claim 1 wherein the protein is a full length human nm23 protein.

* * * * *